United States Patent [19]
Klemp

[11] Patent Number: 5,176,669
[45] Date of Patent: Jan. 5, 1993

[54] TAPELESS SUPER-ABSORBENT DISPOSABLE DIAPER

[75] Inventor: Walter V. Klemp, Houston, Tex.

[73] Assignee: The Veragon Corporation, Houston, Tex.

[21] Appl. No.: 642,756

[22] Filed: Jan. 18, 1991

Related U.S. Application Data

[63] Continuation-in-part of Ser. No. 374,506, Jun. 30, 1989, Pat. No. 5,019,069.

[51] Int. Cl.⁵ .............................................. A61F 13/15
[52] U.S. Cl. .................................................... 604/387
[58] Field of Search .............................. 604/385.2, 387

[56] References Cited

U.S. PATENT DOCUMENTS

| | | | |
|---|---|---|---|
| 3,530,859 | 9/1970 | Heimowitz | 604/391 |
| 4,522,874 | 6/1985 | Pommez | 604/390 |
| 4,680,030 | 7/1987 | Coates et al. | 604/391 |
| 4,699,621 | 10/1987 | Stevens et al. | 604/387 |
| 4,728,326 | 3/1988 | Gilles | 604/391 |
| 4,850,990 | 7/1989 | Huntoon et al. | 604/385.2 |
| 4,900,384 | 2/1990 | Sanders et al. | 604/385.2 |
| 4,937,887 | 7/1990 | Schreiner | 604/385.2 |

*Primary Examiner*—David Isabella

[57] ABSTRACT

A disposable diaper which has a fluid permeable topsheet, a fluid permeable second sheet, a flexible absorbent body, a biodegradable, liquid impermeable barrier including side dams, and a soft, flexible backsheet. The topsheet can include leg cuffs that are an integral, rather than an adjunct, part of the topsheet. The diaper also has an attachment means for allowing the diaper to be secured about the wearer.

4 Claims, 4 Drawing Sheets

TAPELESS SUPER-ABSORBENT DISPOSABLE DIAPER

This application is a continuation-in-part of applicant's co-pending U.S. application Ser. No. 07/374,506 filed Jun. 30, 1989, now U.S. Pat. No. 5,019,069, entitled "Tapeless Super-Absorbent Disposable Diaper."

BACKGROUND OF THE INVENTION

This invention generally relates to absorbent articles and, more particularly, to an improved disposable diaper for incontinent adults and babies.

Infants and other incontinent persons wear disposable diapers to receive and contain feces, urine and other fluid discharges from the body. Disposable diapers function both to contain the discharged materials and to isolate these materials from the body of the wearer and from the wearer's surroundings. Modern embodiments of disposable diaper frequently perform these tasks in a manner superior to that of traditional cloth diapers.

Prior art disposable diapers disclose three basic structural elements: a fluid permeable topsheet designed to be placed next to the wearer's skin; a backsheet which forms, in use, the outer surface of the diaper; and an absorbent element interposed between the topsheet and the backsheet.

The topsheet in prior art diapers is permeable to fluids. The backsheet in prior art diapers is a usually liquid impermeable or repellant. Its function is to contain fluids within the absorbent element thereby protecting the wearer's outer garments and other surfaces from soiling by these fluids. Backsheets are commonly formed of a thin sheet of polyethylene, polypropylene or other flexible moisture impeding materials which are substantially water impervious. However, they are not as soft to the touch as traditional cloth diapers. These materials are also more susceptible to cuts or tears than traditional cloth diapers. One method for overcoming the susceptibility to cuts or tears is to make a thicker backsheet. However, the thicker the backsheet is, the noisier and less biodegradable the disposable diaper is.

The absorbent core of prior art diapers is comprised of a mass of hydrophilic fiber material. These fibers are often formed from cellulose. The core is intended to absorb fluids that permeate the topsheet.

In many disposable diapers, a liquid impermeable or repellant layer or the backsheet is bonded to the inside ends of the absorbent core to form end-dams to prevent fluids from escaping the diaper at the waistline. The manufacturing process which produces the hourglass or form-fitting shape of modern disposable diapers creates the desired shape after all the elements of the diaper have been assembled. This process generally precludes utilizing the liquid impermeable layer to form side-dams to prevent fluids from escaping the diaper in the leg area. The escape of body discharges in the leg area, however, is minimized by using elastic leg cuffs.

Instead of or in addition to an elastic leg cuff, some prior art disposable diapers have standing leg cuffs to minimize the escape of body discharges in the leg area. Because of the manufacturing process which produces the hourglass or form-fitting shape, the standing leg cuffs are separate units bonded to the topsheet.

Almost all prior art disposable diapers utilize tape fasteners attached at the projections ("ears") formed by the widest portions of the hourglass shaped diaper to allow for securing the diaper about the wearer. Because the tape fasteners are indiscriminate as what they will stick to, they can stick to each other, the topsheet, other diapers or equipment during the manufacturing process resulting in unusable product or downtime in the manufacturer's machinery. Similarly, during use, the tapes can stick to areas of the diaper other than those intended and result in an unusable diaper and customer dissatisfaction. In addition, tape fasteners are expensive and non-biodegradable.

SUMMARY

It is, therefore, an object of the present invention to provide an improved absorbent article that has standing leg cuffs. The standing leg cuffs are an integral part, rather than an adjunct part, of the topsheet.

Yet another object of the invention is to provide an attachment means for allowing the diaper to be secured about the wearer.

Therefore, in accordance with one aspect of the present invention, there is disclosed an absorbent article comprising a fluid permeable topsheet, a flexible, absorbent body, a liquid impermeable barrier, and a backsheet comprising soft, flexible material. The impermeable barrier is a film of biodegradable material. In each leg area of the diaper, the topsheet is folded back over itself and bonded thereto to form a casing for elastic and a longitudinal flap which together function as a leg cuff.

In another aspect of the present invention, there is disclosed a disposable diaper comprising a fluid permeable topsheet, an absorbent body, a backsheet, and an attachment means for securing the diaper about its wearer. The means for securing the diaper is applied to one end of the backsheet and to the opposite side of the opposite end of the backsheet.

Other and further objects, features and advantages of the present invention will be apparent from the following description of the presently preferred embodiment of the invention in conjunction with the accompanying drawings.

BRIEF DESCRIPTION OF THE DRAWINGS

The features of this invention which are believed to be novel are set forth with particularity in the appended claims. The invention itself, however, together with its objects and the advantages thereof, will be best understood by reference to the following description taken in connection with the accompanying drawings, in which:

DESCRIPTION OF THE PREFERRED EMBODIMENT

As used herein, the term "disposable absorbent article" refers to articles which receive and contain feces, urine, blood, and other fluid discharges from the body. These articles are intended to be discarded after a single use rather than being laundered or otherwise restored and reused.

A "diaper" is a garment generally worn by infants and incontinent persons. It should be understood, however, that while the present invention is discussed in terms of a diaper, it is also applicable to use in other disposable absorbent articles such as catamenial pads or briefs, absorbent wound dressings and the like.

Figure 1:
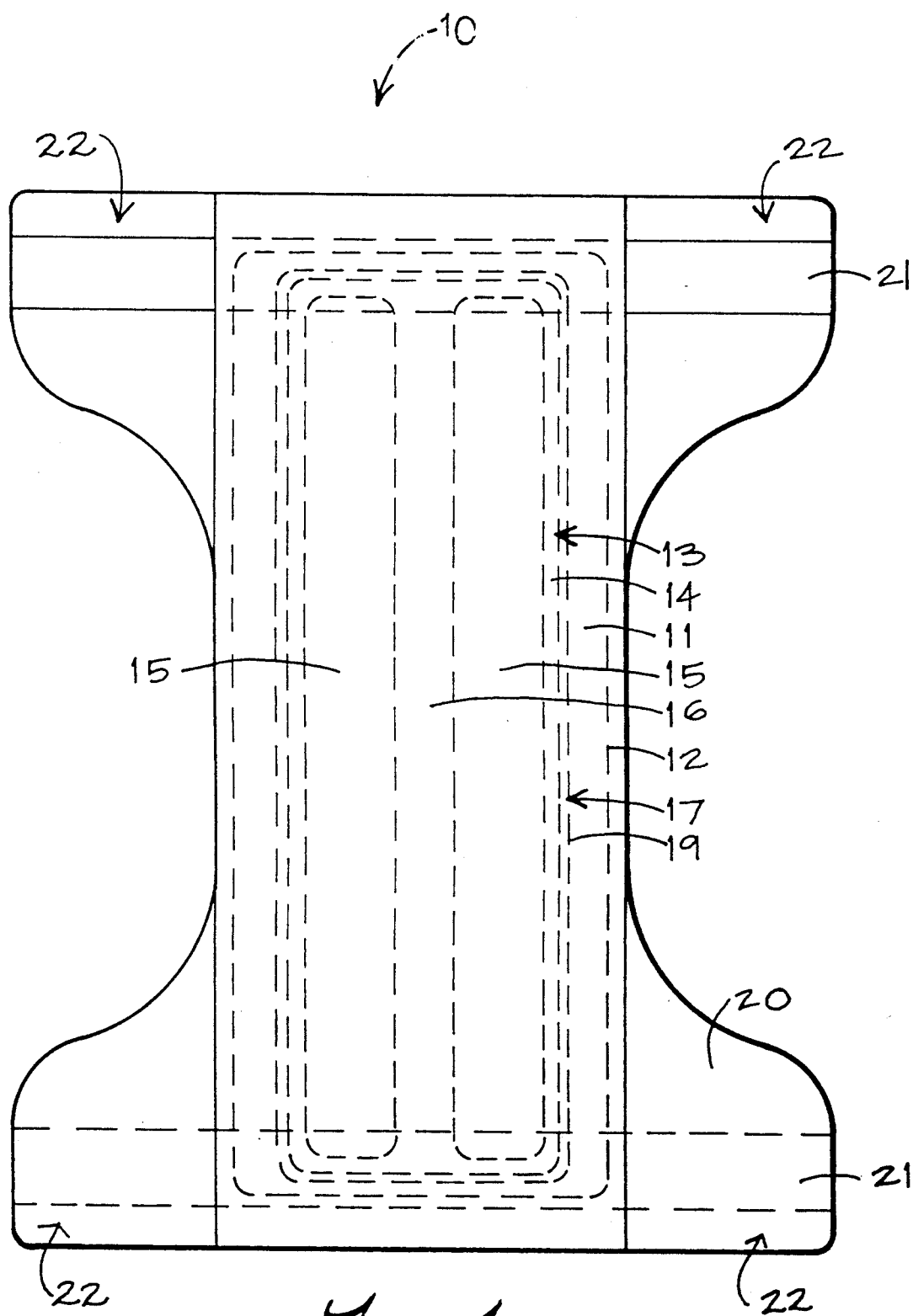
FIG. 1 is an elevational view of a diaper of the invention.
Figure 2:
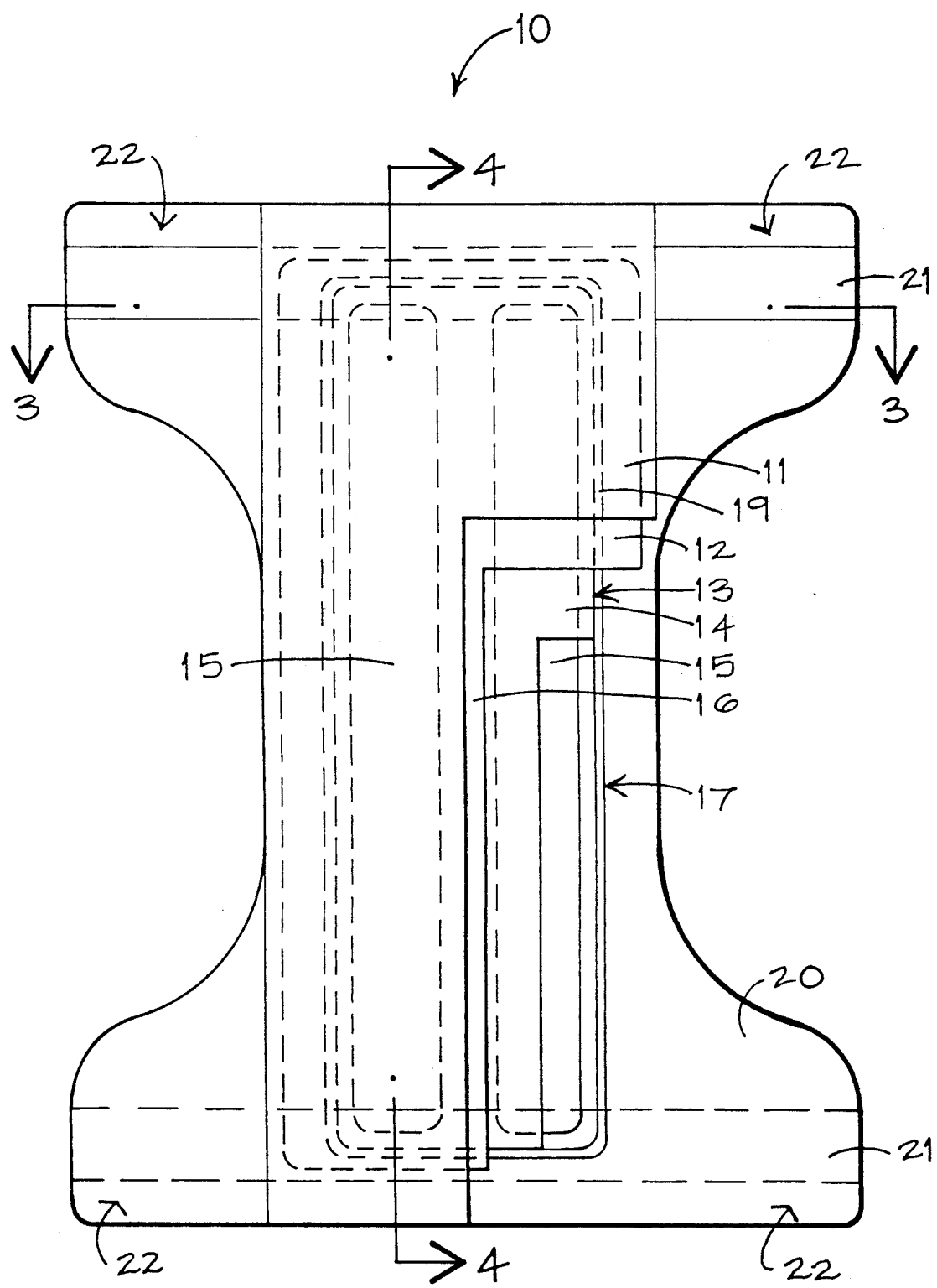
FIG. 2 is an elevational view of a diaper of the invention with portions thereof cut away to show inner detail.

Referring now to the drawings and particularly to FIGS. 1 and 2, the present invention is generally indicated by the reference numeral 10 and generally includes a fluid permeable topsheet 11, a flexible, absorbent body 13, a liquid impermeable barrier 17 and a backsheet 20. A preferred diaper 10 also includes a fluid permeable second sheet 12 interposed between the topsheet 11 and the absorbent body 13.

The topsheet 11 is a relatively hydrophobic, substantially porous, non-woven material and permits a fluid to readily pass into the underlying layers. Its hydrophobicity tends to cause the surface in contact with the wearer's skin to be dry and protected from fluids absorbed within the absorbent element. It can be made in part or completely of synthetic fibers such as polyester, polypropylene and rayon or natural fibers such as cotton. It can be made in a variety of length and width dimensions but is preferably rectangular in shape.

Figure 3:
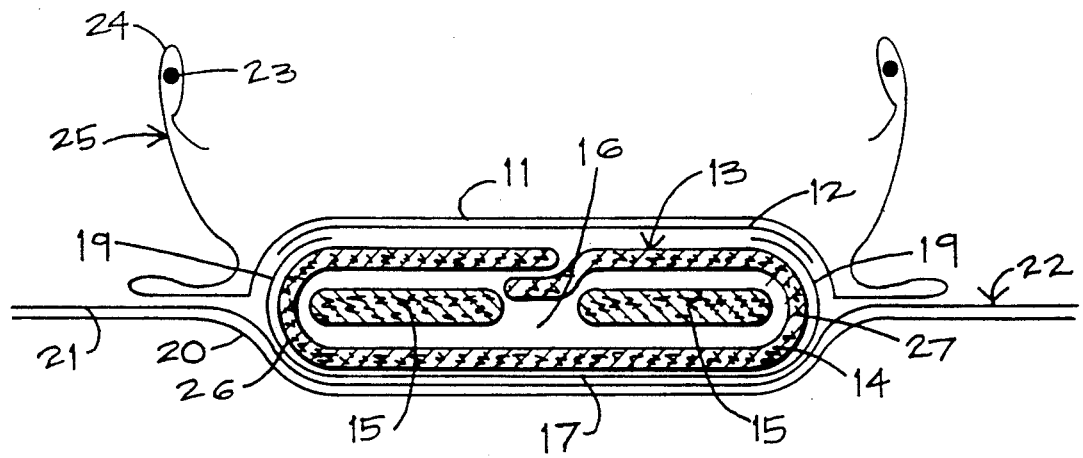
FIG. 3 is a cross section taken along 3—3 of FIG. 2.

In one embodiment shown in FIG. 3, the topsheet 11 is folded back over itself along each of its longitudinal edges and bonded thereto to form casings 24 and an elastic band 23 is positioned within each casing. The topsheet 11 is again folded back over itself intermediate between the center of the topsheet and each longitudinal edge and bonded thereto to form flaps 25.

Figure 5:
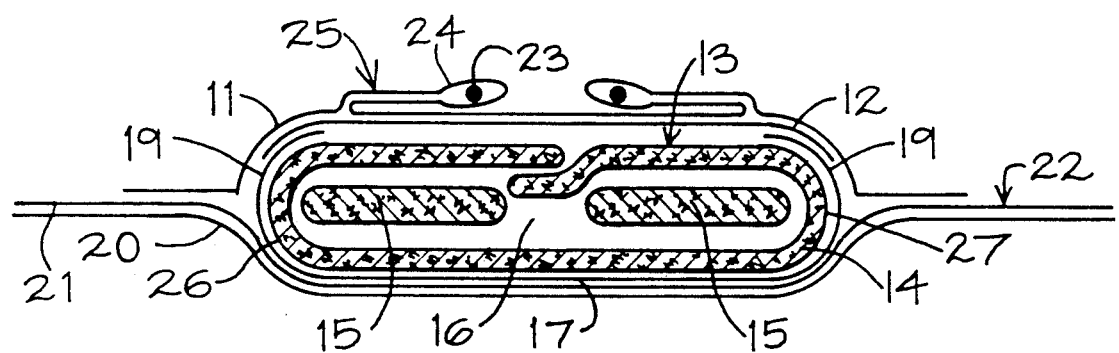
FIG. 5 is a cross section of an alternate embodiment along 3—3 of FIG. 2 with leg flaps folded down.
Figure 6:
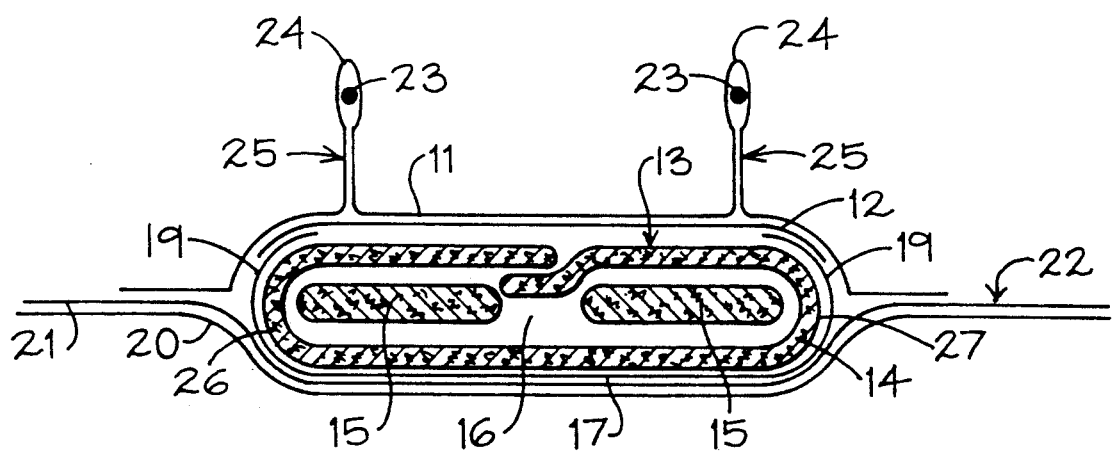
FIG. 6 is a cross section of an alternate embodiment along 3—3 of FIG. 2 with leg flaps erect.

In an alternative embodiment shown in FIGS. 5 and 6, the topsheet 11 is folded back over itself parallel to is longitudinal edges intermediate between said center and each said longitudinal edge and bonded thereto at least once to form both casings 24 and flaps 25. Those skilled in the art will recognize that at least one wide bond or two or more narrower bonds are needed to form both the casings 24 and flaps 25. An elastic band 23 is positioned within each casing 24.

Each longitudinal flap in combination with the adjacent casing and elastic band will form or act as a standing leg cuff to minimize the escape of body discharges in the leg area. The topsheet 11 is bonded to itself by means generally not shown in the figures using any suitable manner known in the art.

The second sheet 12 is substantially porous and permits a fluid to readily pass into the underlying absorbent body 13. This sheet is more or less hydrophobic in comparison with the absorbent body 13 of the diaper and prevents the rewetting of the topsheet 11 by the fluid contained by the absorbent body 13. It can be made of synthetic or natural fibers similar to the topsheet 11. In the preferred embodiment, the second sheet is made of adhesive bonded polypropylene. The second sheet has length and width dimensions generally smaller than those of the topsheet.

The absorbent body 13 essentially contains hydrophilic fiber material. As shown more particularly in FIGS. 3 and 4, it preferably includes an absorbent core 14, at least two super-absorbent zones 15 and at least one wicking zone 16 positioned between the super-absorbent zones. While comminuted wood pulp is preferred for the manufacture of the absorbent core 14, a wide variety of absorbent materials commonly used in disposable absorbent articles, including foams, cellulose and absorbent polymers, can also be used.

Each super-absorbent zone 15 contains super-absorbent hydrogel (SAH) material, preferably super-absorbent polymers (SAP). The SAH is at least partially integrated with materials, preferably, identical to those of the absorbent core 14. In the most preferred embodiment of the present invention, two super-absorbent zones 15 are completely surrounded by and arranged within the absorbent core 14 in substantially parallel zones. The super-absorbent zones 15 are separated by an absorbent area devoid of SAH and referred to as the wicking zone 16.

In the preferred embodiment, absorbent core 14 is folded or wrapped so that the length and width dimensions of the absorbent body 13 are the same or slightly smaller than the second sheet 12. The absorbent body 13 has first and second side edges, 26 and 27 respectively.

Figure 4:
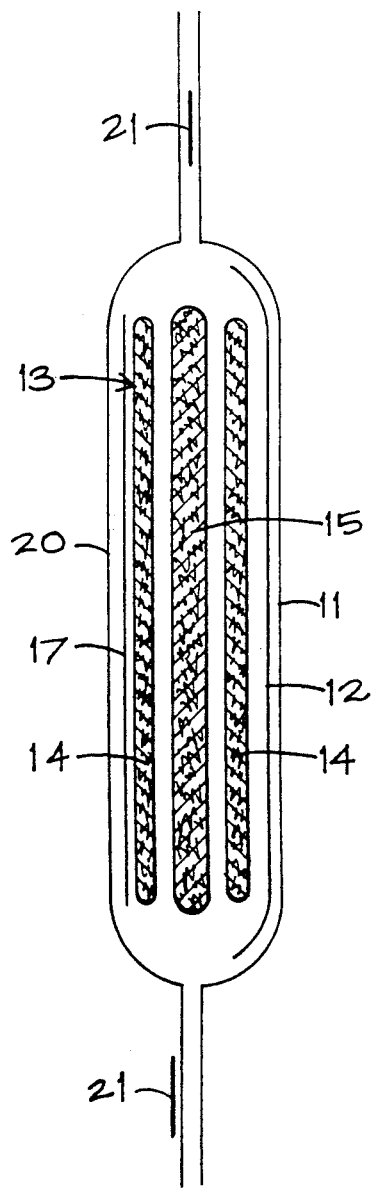
FIG. 4 is a longitudinal cross section along 4—4 of FIG. 2.

The liquid impermeable barrier 17 is a thin film of polyethylene, polypropylene, or other flexible moisture impeding material which is substantially water impervious. A biodegradable polyethylene or polypropylene film with starch, carbon or other non-synthetic additives intended to promote biodegradability can be used. A film formed from 5-20% starch blended with polyethylene and having thickness of 0.6 to 0.8 mil is preferred. As shown in FIGS. 3 and 4, the impermeable barrier 17 folds and extends over the first and second side edges 26 and 27 of the absorbent body 13 forming side dams 19. Preferably the impermeable barrier extends over the absorbent body 13 by 0.5 inches.

The backsheet 20 forms, in use, the outer surface of the diaper and protects the impermeable barrier from cuts and tears. It can be made, exclusively or in combinations, of a wide variety of soft, flexible materials, including polyester, rayon, cotton, polyethylene and polypropylene.

As shown in FIGS. 1 and 2, in the preferred embodiment of the diaper 10 the backsheet 20 is cut in an hourglass or form-fitting shape. It exceeds the width dimension of the topsheet 11 at the "ears" 22 of backsheet but is otherwise coextensive with the topsheet. The top sheet 11 is affixed to the backsheet 20 by means generally not shown in the figures using any suitable method known in the art.

The present invention also includes an attachment means for allowing the diaper 10 to be secured about its wearer. As shown in FIGS. 1 through 4, the preferred embodiment comprises at least one strip of attachment material applied to one end of the backsheet 20 and at least one other strip of the attachment applied to the opposite side of the opposite end of the backsheet 20.

In one embodiment, the attachment material is a biodegradable, selectively adhesive material. The selectively adhesive material can be selected from water-based latex adhesives, hot melt application paraffinor rubber-based adhesives or any other adhesive for which the characteristic of adhesion can be limited to contact with itself or some other selected adhesive. Preferably, the selectively adhesive material is a rubber-based adhesive utilizing a styrene butadiene styrene system such as H4012-01 from Findley Adhesives, Inc. and applied in a 1 to 2 inch strip running the entire width of the backsheet 20. This application of adhesive may be direct, such as via transfer printing or hot melt extrusion, or it may be indirect via application of the adhesive using a film substrate which may be cut to size and bonded to the backsheet In another embodiment, the attachment material 21 is a hook and loop fastening system such as that produced under the Brand VELCRO. Preferably, the VELCRO is applied in a 0.5 to 2 inch strip running the entire width of the back sheet 20. The velcro is applied to the backsheet 20 in any suitable manner known in the art.

The present invention, therefore, is well adapted to carry out the objects and attain the ends and advantages mentioned as well as others inherent therein. The novel features characteristic of this invention are set forth in the appended claims. While a presently preferred embodiment of the invention has been given for the purpose of disclosure, various changes, modifications and alternative constructions to the preferred embodiments described herein will be apparent to those skilled in the art. It should be understood, however, that there is not intention to limit the invention to the specific form disclosed. On the contrary, the intention is to cover all modifications, alternatives, constructions and equivalents falling within the spirit and scope of the invention.

What is claimed is:

1. A disposable diaper, comprising:
   a fluid permeable topsheet, a backsheet and an absorbent body interposed between said topsheet and said backsheet;
   said topsheet includes longitudinal edges and a center wherein said topsheet is folded back over itself along each said longitudinal edge intermediate said center and each said longitudinal edge and bonded at least once thereto thereby forming both casings and flaps which act as fluid dams;
   an elastic band positioned in each said casing;
   said backsheet has first and second side and first and second ends; and
   an attachment means for allowing said diaper to be secured about its wearer comprising at least one strip of a selectively adhesive material applied to said first side adjacent to said first end of said backsheet and at least one other strip of selectively adhesive material applied to said second side adjacent to said second end of said backsheet.

2. The diaper of claim 1, wherein said selectively adhesive material is selected from water-based latex adhesives, hot melt application paraffin- or rubber-based adhesives or any other adhesive having its adhesive characteristic limited to contact with the same or another selected adhesive.

3. The diaper of claim 1, wherein said selectively adhesive material is a rubber-based adhesive utilizing a styrene butadiene styrene system.

4. A disposable diaper, comprising:
   a fluid permeable topsheet, a backsheet and an absorbent body interposed between said topsheet and said backsheet;
   said topsheet includes longitudinal edges and a center wherein said topsheet is folded back over itself along each said longitudinal edge and bonded at least once thereto thereby forming casings and flaps which act as fluid dams;
   an elastic band positioned in each said casing;
   said backsheet has first and second sides and first and second ends; and
   an attachment means for allowing said diaper to be secured about its wearer comprising at least one strip of a hook and loop fastening system applied to said first side adjacent to said first end of said backsheet and at least one other strip of said hook and loop fastening system applied to said second side adjacent to said second end of said backsheet.

* * * * *